Figure 1:
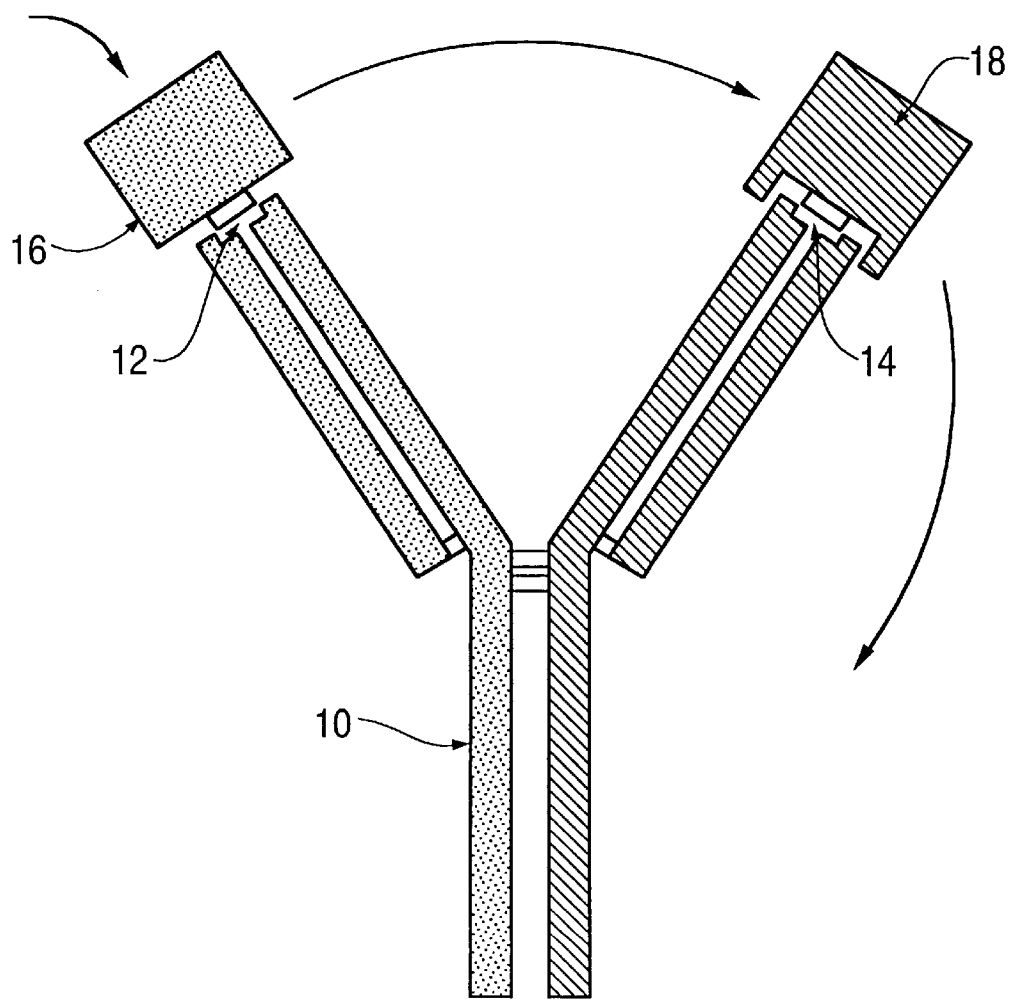

United States Patent [19]
Randle

[11] Patent Number: 5,855,886
[45] Date of Patent: Jan. 5, 1999

[54] ANTIBODIES, AND METHODS FOR THEIR USE

[75] Inventor: Beverley Jane Randle, Bristol, England

[73] Assignee: Surface Active Limited, England

[21] Appl. No.: 459,674

[22] Filed: Jun. 2, 1995

Related U.S. Application Data

[62] Division of Ser. No. 133,079, filed as PCT/GB92/00769, Apr. 24, 1992, Pat. No. 5,573,920.

[30] Foreign Application Priority Data

| Apr. 26, 1991 | [GB] | United Kingdom | 9108954 |
| Apr. 1, 1992 | [GB] | United Kingdom | 9207192 |

[51] Int. Cl.$^6$ .......................... A61K 39/395; C07K 16/00
[52] U.S. Cl. ........................ 424/136.1; 424/178.1; 530/387.3; 530/391.1
[58] Field of Search .............. 424/136.1, 178.1; 530/387.3, 391.1

[56] References Cited

U.S. PATENT DOCUMENTS

| 4,446,233 | 5/1984 | Auditure-Hargreaves et al. | 435/7 |
| 4,578,360 | 3/1986 | Smith | 436/518 |
| 4,686,181 | 8/1987 | Dona | 435/7 |
| 5,273,743 | 12/1993 | Ahlem | 424/858 |
| 5,501,854 | 3/1996 | Raso | 424/136.1 |

FOREIGN PATENT DOCUMENTS

| 0 096 463 | 12/1983 | European Pat. Off. . |
| 0 329 184 | 8/1989 | European Pat. Off. . |
| 0 361 908 | 4/1990 | European Pat. Off. . |
| 0 363 712 | 4/1990 | European Pat. Off. . |
| 2 169 921 | 7/1986 | United Kingdom . |
| WO 83/03679 | 10/1983 | WIPO . |
| WO 90/07714 | 7/1990 | WIPO . |
| 9103493 | 3/1991 | WIPO . |
| WO 91/09134 | 6/1991 | WIPO . |

OTHER PUBLICATIONS

Suresh et al., "Advantages of Bispecific Hybridomas in One–Step Immunocytochemistry and Immunoassays", *Proc. Natl. Acad. Sci. USA*, 83:7989–7993 (1986).

De Lau et al., "Production of Hybrid Hybridomas based on HAT$^s$–Neomycin$^r$Double Mutants", *J. Immunological Methods* 117:1–8 (1989).

*Primary Examiner*—David Saunders
*Attorney, Agent, or Firm*—Banner & Witcoff, Ltd.

[57] ABSTRACT

This invention relates to antibodies and is particularly, though not exclusively, concerned with diagnostic and therapeutic methods' using monoclonal, bi-or tri-specific antibodies. The invention also provides a method in which binding of a first antigen to a first antibody antigen binding site cause release of a second antigen from an adjacent second antibody antigen binding site.

14 Claims, 6 Drawing Sheets

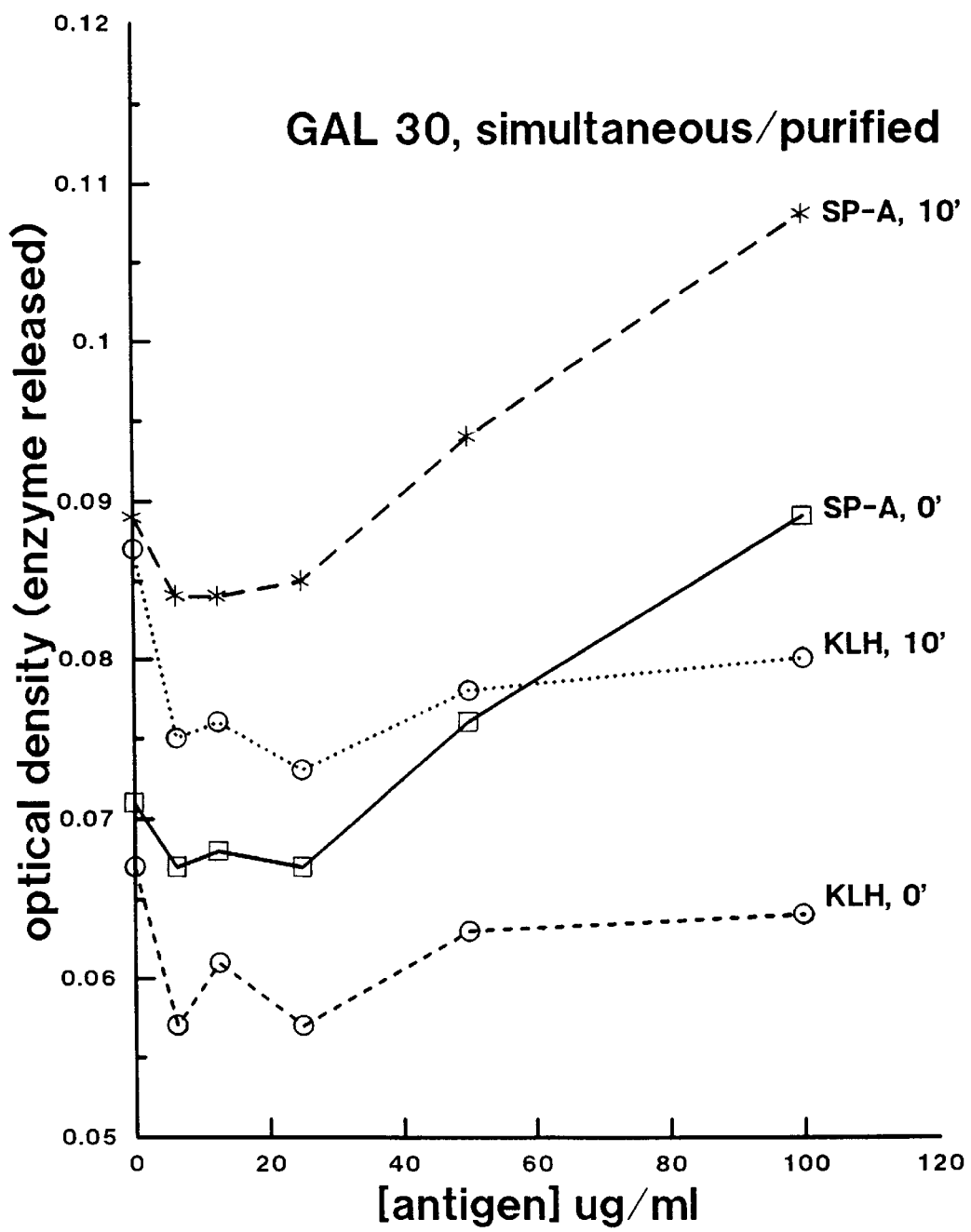

ANTIBODIES, AND METHODS FOR THEIR USE

This application is a division of application Ser. No. 08/133,079, filed as PCT/GB92/00769, Apr. 24, 1992 (U.S. Pat. No. 5,573,920).

This invention relates to antibodies and is particularly, though not exclusively, concerned with diagnostic and therapeutic methods using monoclonal or polyspecific, such as bi-or tri-specific antibodies.

Monoclonal-based antibody assays have not achieved full potential as they generally have to be performed by trained operators in a laboratory. Even relatively simple assays require washing steps and multiple manual addition of reagents. There is a need for a one-step system, which would have a wide field of applications.

Monoclonal antibodies have also found application in treatment of disease. For example, monoclonal antibody conjugates have been used to localize and treat tumours in the body, destroying the tumour with toxic agents, including ricin and radioiodine, attached to the antibody protein.

Bispecific antibodies have been developed from monoclonal antibody technology, in the example of bispecific immunoglobulin G each bispecific antibody has two antigen binding sites of differing specificities. Bispecific antibodies can be produced by fusing two different hybridomas which respectively secrete monoclonal antibodies against the antigens of interest to form a single hybrid-hybridoma or "fusoma", (sometimes called a "polydoma") (Songsivilai, S and Lachmann P. J (1990) Clin Exp Immunol 79, 315 and Suresh M R et al (1986) Proc. Natl Acad Sci USA 83, 7989 and GB2169921A). Parent hybridomas can be removed by standard HAT selection or introduction of selectable drug resistance (De Lau B. M., et al (1989) J. Immunol Methods 117, 1). The first bi-specific antibodies produced were used in a conventional immunoassay (Milstein C., and Cuello A. C., (1983) Nature 305 537). The antibodies were produced by fusing a monoclonal antibody-secreting cell with splenocytes from an immune mouse. The first binding site was specific for an antigen of interest. The second binding site of the enzyme was specific for a marker enzyme. The immunoassay demonstrated increased assay sensitivity, reduction in signal-to-noise ratio, simplification of staining procedures, and preservation of ultrastructural detail.

Bispecific antibodies have found extensive application in novel therapy regimes targeting effector toxins, which remain bound to the antibody, to tumours (Corvalan J. R. F. et al (1987) Cancer Immunol Immunother 24 133), crosslinking cellular antigens on cytotoxic killer cells to tumour targets (Nitta T., et al (1990) Lancet 335 368) and Fanger M. W. and Guyre P. M., Tibtech 9, 375–380 (1991). Other methods of producing bi-and tri-specific antibodies, such as chemical linkage, are reviewed in the latter paper.

WO90/07714 discloses an immunoassay in which an enzyme is stabilised by binding to a bispecific antibody against heat denaturation.

WO91/09134 discloses a bispecific antibody capable of binding both to an enzyme that converts an inactive anticancer prodrug into its active form and to a human cancer cell. An immunocomplex comprising the antibody and the enzyme can be administered to cancer patients together with the inactive prodrug to selectively kill cancer cells with minimal side effects. The enzyme remains bound to the antibody in an active form. Also disclosed are methods of producing polydomas.

It is an object of the invention to provide an immunoassay method involving fewer, preferably only one, reaction steps than conventional immunoassay methods.

According to one aspect of the invention, there is provided a method in which binding of an antigen to one antibody antigen binding site causes release of another antigen from an adjacent second antibody antigen binding site. Whilst not wishing to be bound by theory the applicants believe that steric hindrance between the incoming antigen and the bound antigen causes release of the bound antigen from the second antibody binding site. The first and second antibody antigen binding sites may be provided by the same multispecific antibody or by different antibodies which are physically adjacent. The term "multispecific" embraces all antibodies having more than one antigen binding site such as bispecific and trispecific antibodies. The release of a bound molecule from the second site through binding of another molecule to a first site, may be termed antibody-mediated signal transduction. The term "antibody" used herein embraces immunoglobulins such as IgG, IgA, IgM, IgD and IgE and other proteins having the antigen-binding properties of a naturally-occurring antibody or antibodies produced by recombinant DNA technology or any other such methods.

We have surprisingly found that where antibodies are coated on a microtitre tray at very high concentrations, for example greater than 10–100 $\mu$gml$^{-1}$, as compared to standard concentrations which are typically 1–5 $\mu$gml$^{-1}$, such that the antibodies are arranged in very close proximity to each other binding of an antigen to one antibody antigen binding site can cause release of another antigen bound to an adjacent second antibody antigen binding site. In a preferred embodiment an immunoassay comprises binding antibody to a surface at a concentration of protein of greater than about 20 $\mu$gml$^{-1}$ preferably greater than about 50 $\mu$g ml$^{-1}$.

The second antigen may be bound in an inactive form by the second antibody antigen binding site and released in an active form on binding of the first antigen to the first antibody antigen binding site. The second antigen may be a drug or other therapeutic agent, or an enzyme. The enzyme may be for example $\beta$-galactosidase, or urease.

Monoclonal antibodies have been reported which block the action of cancer therapy drugs. For example antibody NO-1 neutralizes the cytotoxic action of mitozantrone, a potent anti-cancer drug. (Flavell S. U., Flavell D. J. (1991) Br.J.Haematol 78, 330–3). A bispecific antibody in accordance with the invention, with one site directed against a drug, inactivating that drug, will release active drug at the site of expression of the molecule to which a second antigenic site of the bispecific antibody is directed.

Release of the antigen from the second antigen binding site may lead to binding of the released antigen, or one of its reaction products if it is, for example, an enzyme or other catalytic molecule, or a reaction product of a reaction catalysed by it, at a third site on an adjacent antibody causing release of a bound third antigen from an adjacent fourth antigen binding site.

A diagnostic multispecific antibody may induce release of a therapeutic agent in a second "therapeutic" type multispecific antibody by cascade action where the binding of a diagnostic indicator to a first binding site of the first antibody results in release of an enzyme already bound to the first enzyme at a second binding site, the released enzyme or one of its reaction products binding to a second antibody, and this secondary binding event then causes release of a therapeutic agent bound by the second antibody. Binding of a reaction product of the enzyme is preferred as this will produce amplification of the initial binding signal. In a trispecific antibody for diagnostic/therapeutic use which also operates in a cascade action, the first antigen binding site may be directed to the diagnostic marker, the second against an indicator enzyme and the third antigen binding site carrying a therapeutic agent in an inactive form. It will be appreciated that the antibody can be tailored to suit the application. For example an IgM antibody may be used which features ten different reaction steps.

In a preferred embodiment one antigen binding site holds the diagnostic or therapeutic agent in an inactive form by molecular binding at or near the site of indicator/therapeutic activity, such as the active site of a catalytic enzyme or the molecular component essential for therapeutic drug action. In a diagnostic method the second antigen binding site is directed against the molecule under test, be it a marker indicative of a disease or microorganism etc. In the presence of this marker, the agent held in inactive form is released in an active form, resulting from steric hindrance from the close proximity of the two different antibody antigen binding sites. In a therapeutic application the bound inactive agent may be released by presence of the diagnostic molecule or other antigen under test or a molecule or other antigen carried on a bacterium, virus or other microorganism against which treatment is being performed.

Further diagnostic uses of antibodies of the invention include:

Measurement of SP-A in amniotic fluid, pharyngeal aspirate, gut aspirate, blood, tissue section.

Assessment of risk of Respiratory Distress Syndrome, RDS, where absent or low levels of SP-A indicate risk.

Monitoring for appearance of lung function in infants suffering from RDS, adults with adult RDS. Increasing levels of SP-A indicate normal lung function.

Monitoring success of treatment of RDS with artificial surfactant replacement therapy. Return of appearance of lung function is characterised by appearance of SP-A.

The release of two different bound molecules from different antibodies may give a reaction that only occurs when both released molecules are present. A reaction product may bind to a further antibody triggering the release of the substrate, e.g a therapeutic or diagnostic molecule bound to the further antibody. In a therapeutic application, two prodrugs may be released which only become active for treatment when both are present, giving the active drug form. For example, in the treatment of lung cancer a first bispecific antibody has a first antigen binding site directed against lung surfactant apoprotein A ("SP-A") which is expressed by most lung tumours and a second antigen binding site directed against a prodrug A. A second bispecific antibody has a first antigen binding site directed against a transferrin receptor indicative or rapid malignant growth and a second prodrug, prodrug B, in which the combined prodrugs A and B produce an active anticancer complex. In use treatment of a lung cancer patient. with a cocktail comprising the two antibodies having bound prodrugs A and B will result in release of the prodrugs A and B in the presence of SP-A and the transferrin receptor to form the active anticancer complex. In diagnostic applications, the presence of two different diagnostic antigens can trigger a cascade enzyme reaction, the detectable diagnostic indicator product only being produced when both diagnostic epitopes are detected. For example, two bispecific antibodies may be used having first antigen binding sites specific for inhibin A and B chains respectively and second antigen binding sites specific for horse radish peroxidase and glucose oxidase respectively. In the presence of both inhibin A and B chains glucose is converted by glucose oxidase producing peroxide which is then converted by the peroxidase with readily detectable substrate conversion of orthophenyldiamine. In parallel with conventional antigen capture assays in which two different antigenic sites must be detected before a positive result is obtained.

The first and second antibody antigen binding sites may be provided by (i) a mixture of two monoclonal antibodies both at high concentrations, in excess of 20 $\mu$g ml$^{-1}$, preferably, 50 $\mu$gml$^{-1}$, for coating a surface in an immunoassay, (ii) fusoma, secreting parental monoclonal antibodies in addition to a bispecific antibody and (iii) a bispecific antibody, having binding sites for different antigens, purified to homogeneity or produced by chemical modification. Event (i) may be considered as intermolecular transduction, whilst (iii) may be considered as intramolecular transduction. Event (ii) involves inter- and intramolecular transduction.

Diagnostic intermolecular signalling can be achieved economically by a mixture of two preexisting monoclonal antibodies or by standard processing of unpurified bispecific antibody, for example, by affinity chromatography using Protein A or Protein G or ion exchange or gel filtration to isolate secreted immunoglobulin.

Intramolecular antibody signalling requires bi-and trispecific immunoglobulin purified to homogeneity. Purification to homogeneity may be achieved by sequential affinity chromatography steps, using an affinity matrix against which each antigenic site is directed. Thus, the multispecific antibody is purified by chromatography or ion exchange using immobilized enzyme, therapeutic drug or diagnostic molecule.

Cost efficient affinity chromatography may be achieved by using immobilized anti-idiotypic antibody matrixes, where the immobilized antibodies recognize an idiotypic determinant of the multispecific antibody undergoing purification to homogeneity.

According to another aspect of the invention there is provided an immunoassay method for determining the presence or absence of an antigen in a sample, the method comprising contacting the sample with a multispecific antibody having binding sites for the antigen and an enzyme, binding of the enzyme to the antibody inactivating the enzyme, in which binding of the antigen to the antibody results in release of bound enzyme from the antibody in an active form from the antibody and detecting the activity of the released active enzyme which indicates the presence of the antigen in the sample. Thus this aspect of the invention provides a simple immunoassay method involving a single reaction step.

Whilst not wishing to be bound by theory the applicants believe that steric hindrance between the incoming antigen and the bound enzyme causes release of the enzyme from the antibody. Therefore the enzyme is typically chosen on the basis of its size to facilitate steric hindrance with the antigen of interest. The antibody used should bind the enzyme in a sufficiently stable manner to ensure that the enzyme does not become unbound in the absence of the antigen. Preferably the enzyme is bound to the antibody by its active site.

The antigen may be for example SP-A, a lack of which is indicative of a risk of Respiratory Distress Syndrome occurring in the preterm premature infant (Hallman et al (1988) Am J Obs Gynecol 158, 153). This respiratory condition affects 2% of all newborn babies and is the most common cause of death in normally-formed babies in the first week of life.

The enzyme may be for example $\beta$ galactosidase, glucose oxidase, urease, carbonic anhydrase, or horseradish peroxidase, all of which are well characterised and easily assayable enzymes.

According to another aspect of the invention there is provided a multispecific antibody having binding sites for an antigen and an enzyme in which the enzyme is inactivated by binding to the antibody and is released from the antibody in an active form through binding of the antigen to the antibody. Preferably, the antibody is bispecific.

According to another aspect of the invention there is provided a method of detecting SP-A in a sample of mammalian body fluid comprising contacting the sample with a multispecific antibody having binding sites for SP-A and an enzyme, binding of the enzyme to the antibody inactivating the enzyme, in which binding of SP-A to the antibody results in release of enzyme in an active form from the antibody and detecting the presence of the released active enzyme which indicates the presence of SP-A in the sample. The enzyme may be β-galactosidase.

According to another aspect of the invention there is provided an immunoassay method for determining the presence or absence of an antigen in a sample, the method comprising contacting the sample with a first bispecific antibody having binding sites for the antigen and a first enzyme, a reaction product of the first enzyme acting as a substrate for a second enzyme at a second site which catalyses a readily-detectable reaction indicating the presence of the antigen in the sample. The first enzyme may be glucose oxidase. The second enzyme may be horseradish peroxidase.

Any diagnostic method in accordance with the invention may be arranged to be carried out in a biosensor in which the multispecific antibody acts as the biological sensing element of the biosensor. Hitherto monoclonal antibodies have been used in electrode biosensors to detect human gonadotrophin (Robinson G. A. et al (1987) Biosensors 3, 147) and *Staphylococcus aureus* in food (Mirhabibollahi B., et al (1990) J. Appl. Bacteriol 68, 577). General application has, however, proved impossible as detector antibodies must be removed by washing before measurement of antibody-bound antigen and also problems exist with enzyme regeneration. As the methods of the invention use an integral enzyme the bispecific antibody can be incorporated directly into electrodes and semiconductor transducers. For example an oxygen electrode or an ion selective field effect transistor (ISFET) may include a bispecific antibody to which is bound glucose oxidase; or a urea electrode, or a chemically sensitive field effect transistor (CHEMFET) may include a bispecific antibody to which is bound urease.

Examples of enzymes and the preparation of multispecific antibodies which may be used in the method of the invention are now described below by way of example only. β-galactosidase is well characterised and its activity can be easily assayed.

Glucose oxidase is isolated at low cost from *Aspergillus niger* and has a molecular weight of 186 kD. Glucose oxidase is a mannose-rich glycoprotein and consequently can be cross-linked to increase the local concentration of bound inactive enzyme through the mannose carbohydrate chain with retention of enzyme activity. (Kozulic B. et al (1987) Appl Biochem Biotechnol 15, 265). The size of glucose oxidase polymers can be controlled by the chemical reaction. Glucose oxidase can be used as the enzyme component of an oxygen electrode.

Urease, which can be isolated from Jack beans at low cost, is a hexameric protein of 590 kD, with one active site in each 96 kD subunit. Urease is used as the enzyme component in the urea electrode.

Carbonic anhydrase is a monomeric enzyme with a relatively low molecular weight of 29 kD. Carbonic anhydrase catalyses carbon dioxide hydration and hydrogen carbonate dehydration and can be isolated from human red blood cells at low cost.

Horseradish peroxidase has a well characterised heme site (La Mar G. N. et al (1980) J Biol Chem 255, 6646). Horseradish peroxidase may be used in a two site immunoassay method with glucose oxidase at a first site and horseradish peroxidase at a second site to produce an enzyme cascade with the hydrogen peroxide produced by glucose oxidase acting as a substrate for horseradish peroxidase.

Figure 2A:
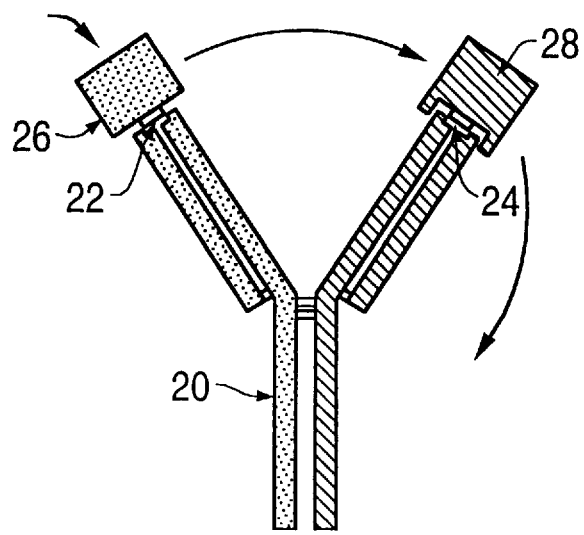
Figure 2B:
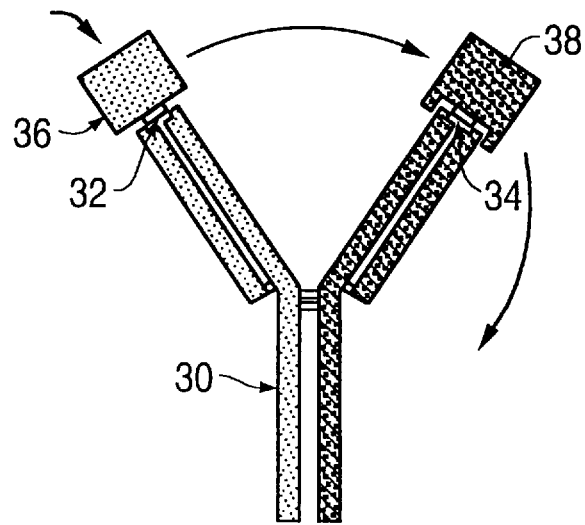
Figure 2C:
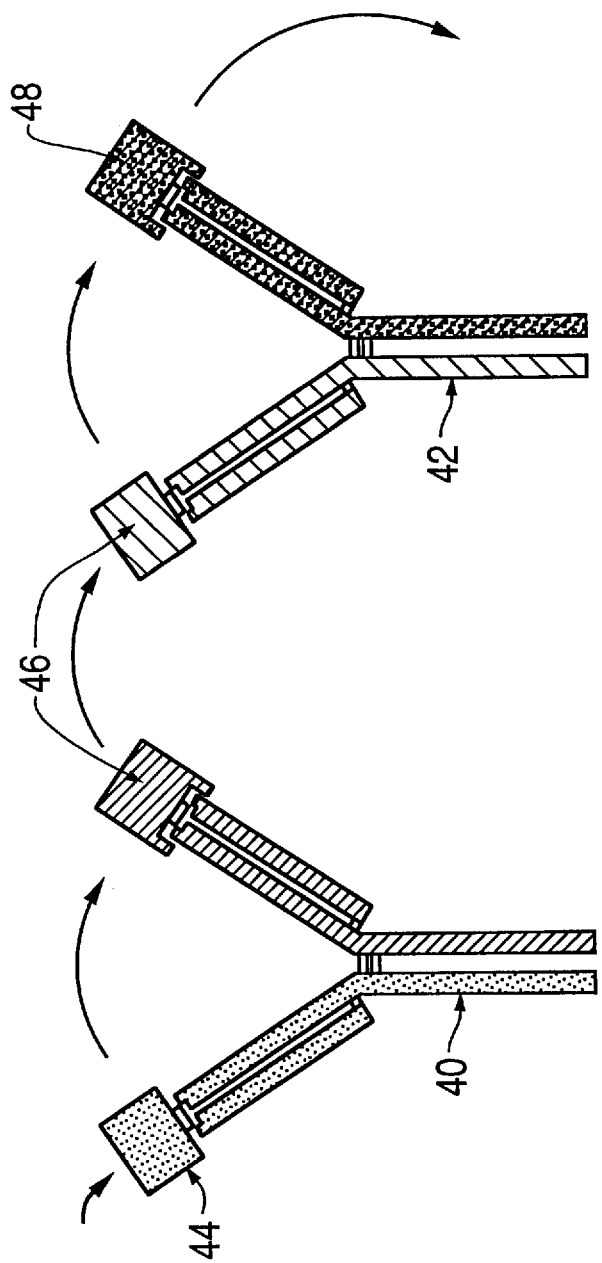

The preparation of antibodies in accordance with the invention and methods of their use will now be described, by way of example only with reference to the accompanying FIGS. 1 to 5 in which:

FIG. 1 illustrates the operation of an antibody in accordance with the invention;

FIGS. 2A, 2B and 2C illustrate applications of antibodies in accordance with the invention; FIG. 2A shows a diagnostic embodiment employing a bispecific antibody which binds analyte and enzyme. FIG. 2B shows a therapeutic embodiment employing a bispecific antibody which binds a cancer cell surface antigen and an anti-cancer drug. FIG. 2C shows a combined diagnostic/therapeutic application employing two bispecific antibodies. One antibody binds both a cancer cell antigen and an enzyme. The other antibody binds the enzyme or a reaction product thereof, as well as a anti-cancer drug.

Figure 3:
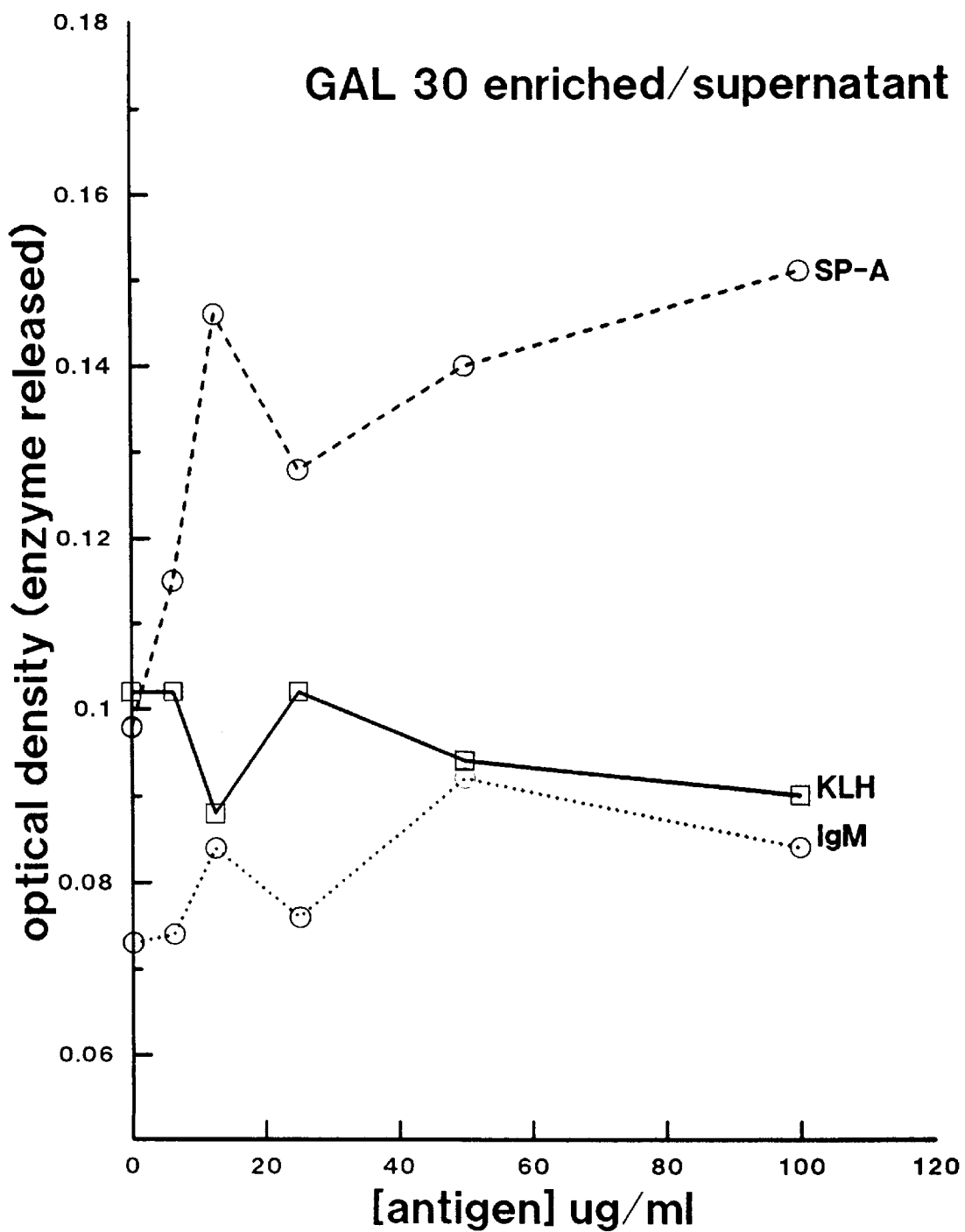
Figure 4:
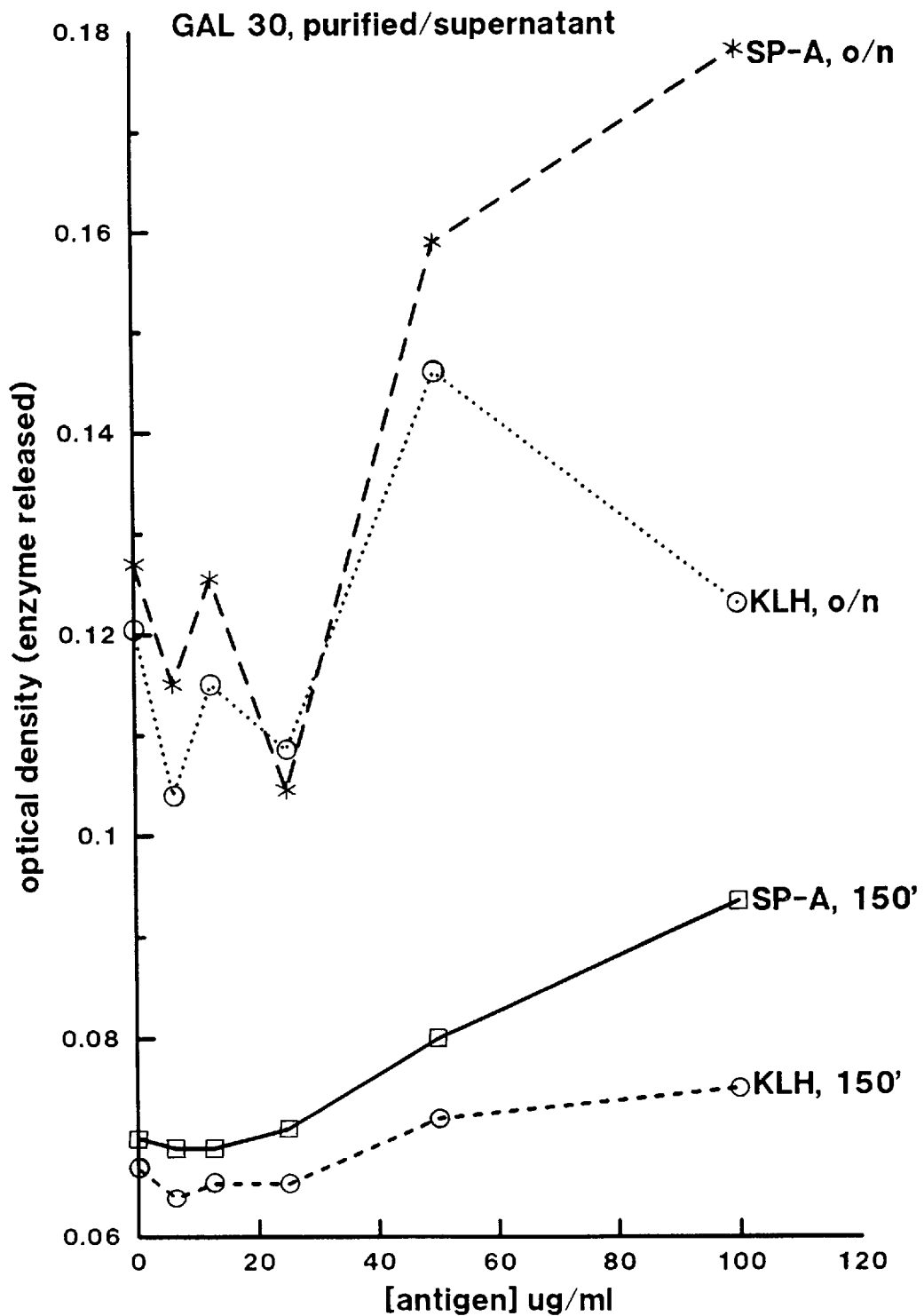

FIG. 3 is a graph illustrating the activity of enzyme released from an antibody in accordance with the invention; and FIG. 4 is a graph illustrating the activity of enzyme released from an antibody in accordance with the invention; and FIG. 5 is a graph illustrating the activity of enzyme released from an antibody in accordance with the invention.

The bispecific antibody 10 of immunoglobulin G type shown in FIG. 1 comprises first and second binding sites 12 and 14 which bind in use first and second antigens 16 and 18 respectively. Binding of the first antigen 16 to first antigen binding site 12 causes release of bound second antigen 18 from the second binding site 14.

In the diagnostic application shown in FIG. 2A) bispecific antibody 20 has first and second antigen binding sites 22,24 directed respectively to an analyte of interest 26, e.g. SP-A and to an enzyme 28 which has readily detectable substrate conversion activity e.g. β-galactosidase. The enzyme is inactivated when bound to the antibody at the second binding site 24 for example by binding through or adjacent its active site or through alteration of the active site's configuration.

Binding of the analyte 26 from a sample to the first binding site 22 causes release of the bound enzyme 28 into the media where it's activity can be readily detected indicating presence of the analyte.

In the therapeutic application illustrated in FIG. 2B) bispecific antibody 30 has first and second antigen binding sites 32,32 directed respectively to an antigen on the surface of a cancer cell 36, and to an anti-cancer drug 38. The drug 38 is inactivated when bound to the antibody at the second binding site 34. Binding of the antigen 36 to the first binding site 32 causes release of the bound drug 38 in an active form whereupon it can act against the cancer cell expressing antigen 36.

In the combined diagnostic/therapeutic application shown in FIG. 2C) two different bispecific antibodies 40,42 are used. Antibody 40 has specificity for an antigen 44 carried by a cancer cell and for an enzyme 46 which it binds in an inactive form. Antibody 42 has specificity for an anticancer drug 48 and for the enzyme 46 or a reaction product of the enzyme. Binding of the antigen 44 to antibody 40 causes release of the enzyme 46 in an active form. The activity of the released enzyme can be readily detected. The enzyme 46 or one of its reaction products then binds to the second antibody 42 which causes release of the drug 48 in an active form to kill the cancer cell expressing antigen 44.

Bispecific antibodies are conveniently prepared by hybridoma cell fusion technology. First suitable monoclonal antibody secreting hybridoma cells are isolated and characterised. Next the parental cell lines are rendered drug resistant by growth in various selection media. These drug resistant clones can then be used for bispecific antibody production by cell fusion between parental cell lines of differing drug resistant or between a drug resistant hybridoma and splenocytes from an immune mouse. After cell fusion and selection, cultures are screened for production of antibodies of the desired reactivities. Chosen cultures are cloned and secretion of bispecific immunoglobulin by the fusoma confirmed by immunoassay.

For use in the current invention, secreted immunoglobulin is enriched by protein A affinity chromatography. The enriched antibody is then subjected to sequential affinity chromatography steps to isolate homogeneous bispecific immunoglobulin.

PREPARATION OF BISPECIFIC ANTIBODIES

A) Preparation of hybridomas secreting suitable monoclonal antibodies

Bispecific antibodies are conveniently prepared by fusoma technology. First, monoclonal antibody-secreting cell lines are isolated against the enzymes of interest and against the cytotoxic drug methotrexate.

Methotrexate is coupled to ovalbumin for increased immunogenicity on antigen (enzyme) presentation. For immunisation, enzymes are used in native form and in conyugates with keyhole limpet haemocyanin, for enhanced immunogeneicity. Serum responses of immunised BALB/C mice are monitored and on generation of a suitable response hybridomas are prepared by cell fusion of splenocytes from immune mice to mouse SP2/0 myeloma cells. Hybridomas are screened initially against the target antigen or methotrexate conjugate by enzyme-linked immunosorbent assay (ELISA). Monoclonal antibodies produced by cloned hybridomas secreting the antibodies against the enzymes are then screened for ability to block enzyme-mediated substrate conversion reactions. Monoclonal antibodies having the ability to block such reactions may do so through binding to or near the active site. Methotrexate-reactive antibodies are screened for their ability to block the cytotoxic effect of methotrexate.

Hybridomas producing suitable monoclonal antibodies are then cultured in toxic media to isolate drug resistant clones suitable for fusoma production.

Two selectable markers are employed to develop suitable drug resistant clones for fusoma production. Hybridomas are cultured in 5 $\mu$g per ml. of 6-thioguanine, to select hypoxanthine guanosine phosphoribosyl transferase deficient variants.

To induce thioguanine resistance $4 \times 10^7$ hybridoma cells were dispersed into $6 \times 48$ well tissue culture plates containing alpha MEM medium (Stanners C. P., Eliceri G. and Green H. 1971, Nature, New Biol 230, 52) with 10%(V/V) heat inactivated foetal calf serum (FCS), 20% (V/V) conditioned medium from J774 macrophage cell line (Cancer Research 1977 37, 546) and 5 $\mu$g per ml of 6-thioguanine (Sigma A4660). After approximately 3 weeks, clonal outgrowths of drug resistant clones were visible. Clones were removed by pipette and subcultured. Antibody secretion was confirmed and selected cultures stored. These variants are then selected against in the standard HAT selection system (Littlefield J. W., (1964) Science 145, 709).

Drug resistant cells are also selected by culture in increasing concentrations of the cardiac glycoside ouabain which inhibits the sodium potassium ATPase of the mammalian plasma membrane. Wild type cells die in the presence of ouabain whilst resistant clones can grow in 180-fold excess concentration of the drug (Mankovitz R. et al (1974) Cell 3, 221).

To induce ouabain resistance, $2 \times 10^6$ hybridomas were grown and subcultured at confluence in alpha MEM, 10% (v/v) FCS in increasing concentrations of ouabain (Sigma 03125) from 1 $\mu$M to 0.5 mM.

To induce double drug resistance (ie to ouabain and thioguanine)cells were grown in increasing concentrations of ouabain as above. Once capable of growth in 0.5 mM ouabain medium, drug resistance to 6-thioguanine was induced as described above.

Hybridomas resistant to 6-thioguanine and to ouabain are cloned ready for fusoma production.

B) Fusoma Production

Fusomas secreting bispecific antibodies are produced by conventional techniques in a series of cell fusion experiments to select those producing bispecific antibodies with an enzyme-reactive arm and a second antibody binding site recognising the antigen of interest. The fusomas are derived from "enzyme-reactive cells", whether splenocytes from immune mice or hybridomas, and from "antigen reactive cells". Examples of antigen reactive cells include those producing the antibodies A15, recognising ovalbumin of 43 kD, KLH1, recognising keyhole limpet haemocyanin of 800 kD and D4 and E8 both of which react with human lung surfactant apoprotein A (SP-A) (Randle B. J. et al (1992) in preparation). Antibody E8 is thought to be similar to antibody PE10 described in Kuroki Y. et al Am. J Pathol 1986 124; 25–33. Cell fusion experiments are performed in three series:

1. Fusion of thioguanine resistant, HAT sensitive hybridomas antigen reactive or enzyme reactive to splenocytes of immune mice enzyme-reactive or antigen reactive selection by HAT.

2. Fusion of thioguanine resistant hybridomas either antigen or enzyme-reactive to ouabain resistant hybridomas, either antigen or enzyme-reactive selection by ouabain thioguanine medium.

3. Fusion of double resistant thioguanine/ouabain hybridomas either antigen or enzyme reactive to wild type hybridomas either antigen or enzyme reactive with selection in HAT ouabain medium.

Cell fusions are performed by standard techniques. Thioguanine-resistant hybridomas are mixed with splenocytes from immune mice in the ratio 1:10 cells respectively (series 1) and fusoma cells prepared by incubation in 50% (w/v) polyethylene glycol 1500 in serum free medium for 75 seconds. The cell fusion event is terminated by timed addition of serum containing growth medium. The fusomas are then plated out in multiwell plates, up to 800 separate cultures, and grown in HAT selection medium for two weeks.

Where fusomas are produced by fusion of two preexisting hybridomas with differing selectable markers (series 2) the cells are mixed in a 1:1 ratio prior to fusion. The fusion event is performed in 50% (w/v) polyethylene glycol 1500 in serum free medium for 75 seconds. The reaction is terminated by timed addition of serum containing medium over 5 minutes. Fusomas are plated out in 200 separate cultures in multiwell plates and in selection medium containing 5 µg per ml thioguanine and 0.5 mM ouabain. Cultures are inspected for growth after two weeks in incubation at 37° C., 5% $CO_2$ (v/v) in air.

Where fusomas are produced by fusion of double drug resistant hybridomas to wild type hybridomas (series 3) the cells are mixed in a 1:1 ratio prior to fusion. The fusion event is performed in 50% (W/V) polyethylene glycol 1500 in serum free medium for 75 seconds. The reaction is terminated by timed addition of serum containing medium over five minutes. Fusomas are plated out in 200 separate cultures in multiwell plates and in HAT selection medium containing 0.5 mM ouabain.

Cultures are then screened for recognition of the enzyme or methotrexate. Reactive cultures are then tested for recognition of the chosen antigen. Cultures are screened by enzyme-linked immunosorbent assay (ELISA) for secretion of antibody reactive with the antigen of choice. Antigen is immobilised on 96-well multiwell plates at a concentration of 5–10 $µgml^{-1}$ by incubation overnight at 4° C. in 0.1M carbonate buffer pH 9.6, 50 µl per well. Plates are blocked with 100 µl per well 10% (v/v) fetal calf serum in phosphate buffered saline (PBS) for 2 hrs at room temperature. Culture supernatants under test are loaded in duplicate at 50 µl per well and incubated for 1 hr at room temperature. The plates are washed with 0.05% (v/v) Tween 20 in PBS and bound antibody is detected using a second layer enzyme-conjugated antimouse immunoglobulin antibody with subsequent detection for enzyme substrate conversion. Cultures identified as secreting bispecific antibodies are then cloned by standard techniques of limiting dilution and single cell manipulation and grown up to produce milligramme quantities of the secreted immunoglobulins. The secreted antibodies are then characterised by ion exchange chromatography (Wong J. T. and Colvin R. B. (1987) J. Immunol. 139, 1369) and purified for experimental diagnostic use. In the present example, affinity chromatography was used for immunoglobulin purification.

Preparation of Assay

Bispecific immunoglobulin or enriched immunoglobulin secreted by fusomas is immobilized on multiwell plates by incubation in ELISA coating buffer. Plates are blocked with 10% (V/V) FCS in PBS. The antibody is then loaded with enzyme by incubation with enzyme containing media. Unbound enzyme is removed by washing and the antibody enzyme complex is then ready for use.

The complex is used in two different ways to measure antigen. First antigen is added for 15 minutes, the supernatant removed and this supernatant then assayed for the presence of enzyme activity released from the complex. Secondly, in simultaneous one step format, the enzyme substrate is added to the complex at the same time as the antigen. In both cases, enzyme activity is measured directly by the colour change associated with substrate conversion is indicative of the presence of antigen in the sample.

For example, lung surfactant apoprotein A purified by density-dependent centrifugation (Katyal S. L. and Singh G. (1979) Lab Invest 40 562) is used to calibrate the assay. Samples of amniotic fluid from premature deliveries are then assayed for apoprotein concentration.

Bispecific Antibody Demonstrating Antibody-Mediated Signal Transduction

Fusoma cell line GAL 30.19 secretes a bispecific immunoglobulin reactive with SP-A and β-galactosidase (from *Escherichia coli*). The cell line was isolated from a cell fusion event between 6-thioguanine resistant D4 hybridoma (Randle et al 1992 in preparation), subclone D4tg13 secreting an antibody reactive with SP-A and splenocytes from a BALB/c female mouse immunized weekly over an eight week period with 10 µg per dose of beta-galactosidase (Sigma G5635) supported with an alum adjuvant. 20 µg of beta-galactosidase was given intravenous four days prior to the cell fusion experiment.

Cell fusion was performed by standard techniques and resulting cell mixture was plated in HAT selection medium. Cultures were screened 17 days later. 714 fusoma cultures were obtained, 41 of which were found to secrete antibody reactive with beta-galactosidase by indirect ELISA. 8 cultures secreted immunoglobulin reactive with both SP-A and beta-galactosidase as determined by Western Immunoblot. These cultures were cloned by limited dilution and 6 clonal cultures were selected for further study. One of these cell lines GAL 30.19 is now described. A sample of GAL30.19 was deposited in accordance with the provisions of the Budapest Treaty at the European Collection of Animal Cell Cultures, Porton Down United Kingdom on 22nd Apr. 1992 and has been accorded the accession number 92042211.

The cell line was routinely grown in alpha HAT medium and produces approximately 5 µg per ml of immunoglobulin in unstirred monolayer culture growth conditions.

Enriched GAL 30.19 immunoglobulin was isolated by standard affinity chromatography techniques using Protein A Sepharose (Sigma P3391). Briefly, 1.2 litres of culture supernatant was adjusted to pH8.2 by addition of 1M Tris HCl, pH8.5; and run on to a 6 ml Protein A sepharose column. After washing with 10 volumes of PBS, adjusted to pH8.2 by addition of 1M Tris HCl, pH8.5, bound immunoglobulin was eluted by use of sodium citrate buffer, pH3.5 0.1M. 1 ml fractions were immediately neutralized with 700 µl of 1M Tris HCl pH8.5. Protein concentrations of the eluted fractions were determined by Coomassie Blue dye binding assay and antibody titre estimated by indirect ELISA. 6.05 mg of immunoglobulin was isolated from 1.2 litres of culture medium. Antibody titre of the most concentrated fraction was $1:10^6$ for beta-galactosidase and $1:10^5$ for SP-A by indirect ELISA.

Antigen Capture to Demonstrate Recognition of Both Beta-Galactosidase and SP-A

Enriched GAL30.19 can be used in an antigen capture ELISA format to detect beta galactosidase and SP-A. Briefly, immunoglobulin was coated at 5 µg per ml in carbonate-bicarbonate buffer, pH9.6, 50 µl per well, in a 96 well flat bottom immunoassay plate (Falcon Cat No. 3912) overnight incubation at 4° C. Plates were blocked with 100 µl per well, 10% (v/v) FCS in PBS, 2 hours at room temperature.

Beta Galactosidase Antigen Capture

Increasing concentrations of beta galactosidase were loaded in 50 µl volumes, from 0–100 µg per ml, and incubated for 1 hour at room temperature. Wells were washed twice with 200 µl PBS 0.5% (v/v) PBS Tween 20 and then bound beta galactosidase was detected by addition of enzyme substrate, "beta galactosidase substrate buffer".

The substrate comprised 20.5 mg of O-nitrophenyl β-D-galactopyranoside (Sigma N-1127; ONPG) dissolved in 1 ml of 0.1M pH 7.3 phosphate buffer with gentle warming. 832 μl of ONPG solution was added to 5 ml of phosphate buffer containing bsa and magnesium chloride in the ratio of:

2.7 ml 0.1M pH 7.3 phosphate buffer:

0.1 ml 0.03M magnesium chloride with 0.5% (w/v) bovine serum albumin (bsa).

In antigen capture format, GAL 30.19 detected a minimum of 5 μg per ml of beta galactosidase.

SP-A Antigen Capture

Concentrations of SP-A, from 5 to 100 μg per ml, were loaded in 50 μl volumes and incubated for 1 hour at room temperature. Wells were washed twice with PBS Tween 20 and bound SP-A detected by addition of 50 μl per well 1:30 E8 biotin in PBS. E8 hybridoma secretes a monoclonal antibody reactive with a second, distinct from D4, epitope of SP-A (Randle et al 1992 in preparation). E8 immunoglobulin was substituted in the approximate ratio of 3 biotin molecules per immunoglobulin: Stock E8-Biotin was 1 mg per ml for dilution). After incubation for 30 minutes, plates were washed twice with PBS Tween and wells were then incubated with 50 μl of 1:500 Avidin-alkaline phosphatase in PBS (1 mg per ml stock in PBS: Sigma A2527) for 30 minutes at 4° C. Wells were washed three times with PBS Tween and then presence of alkaline phosphatase was detected by substrate conversion of para-nitro phenyl phosphate, disodium hexahydrate (Sigma 104–105E). Briefly, 50 μl per well of the substrate was added at 1 mg per ml in 1M diethanolamine buffer pH9.8, "alkaline phosphatase-substrate". The alkaline phosphatase substrate buffer comprises diethanolamine buffer 10% (v/v), consisting of 97 ml diethanolamine, 800 ml water, 100 mg of magnesium chloride hexahydrate. 1M hydrochloric acid is added until the pH is 9.8, volume is then made up to 1 litre with water. Stored in dark at 4° C. until use. Substrate conversion by enzyme was detected by measurement of optical density at 410 nm. Using this antigen capture format, GAL 30.19 can detect a minimum of 6.25 μg per ml SP-A.

GAL30.19 Blocks the Activity of Beta Galactosidase

50 μl enriched GAL30.19 immunoglobulin at 1 mg per ml was added to 50 μl of beta galactosidase solution in PBS, concentration of 500 μg per ml. 100 μl of beta galactosidase substrate was added and substrate conversion was monitored at 410 nm. A control experiment using 50 μl of PBS in place of the antibody solution was performed in parallel. After 5 minutes, optical density of the enzyme product was 0.920 in the absence of antibody and 0.597 in the presence of GAL30.19 in the test sample. This demonstrates that GAL30.19 blocks the-enzymic activity of beta galactosidase.

Purification of Bispecific GAL30.19 Immunoglobulin to Homogeneity

Homogeneous bispecific immunoglobulin was isolated from enriched antibody by sequential affinity chromatography. The method of choice is sequential Affinity Chromatography. The immunoglobulins carrying the first antigenic site were isolated by affinity chromatography using a bead matrix carrying purified SP-A. Elution was performed using standard diethylamine pH11, 1M, buffer and fractions neutralized with Tris-HCl, pH8, 1M. The neutralized fractions were "desalted" by buffer exchange to PBS using G25 Sephadex (trade mark) filtration. The samples were then subjected to a second affinity chromatography step, using a chromatography gel where the gel matrix carries a bead matrix carrying β-galuctosidase. DEA elution was performed and the homogenous bispecific antibody desalted and stored in PBS 0.02% azide at 4° C. until used. On completion of the chromatography 2.7 mg of enriched immunoglobulin yielded 0.38 mg of homogeneous immunoglobulin. Antibody titre of the most concentrated fraction was $1:10^4$ for beta galactosidase and $1:10^3$ for SP-A. Presence of heavy and light chain polypeptides of GAL 30.19 was confirmed by electrophoresis of the homogeneous sample in 10% (w/v) SDS PAGE under reducing conditions.

Demonstration of Antibody-Mediated Signal Transduction

Transducing antibody activity has been demonstrated both with enriched GAL 30.19 immunoglobulin, isolated by Protein A affinity chromatography and with purified immunoglobulin, isolated to homogeneity from enriched antibody by sequential affinity chromatography on SP-A Sepharose and beta galactosidase Sepharose.

EXAMPLE 1

Enriched Immunoglobulin Assay. (See FIG. 3)

Enriched GAL30.19 immunoglobulin was coated at 50 μg per ml in ELISA coating buffer, carbonate/bicarbonate pH9.6, 50 μl per well, overnight at 4° C. Plates were blocked with 100 μl per well of 10% (V/V) FCS in PBS, 2 hours at room temperature. Wells were then incubated with 50 μl of 20 μg per ml beta galactosidase (Sigma G5635) in wash buffer, PBS with 0.5% (W/V) bsa (Sigma A7888) for 1 hour at room temperature. Wells were then washed with 2 washes of 200 μl PBS Tween 20 (0.05% V/V), to remove unbound enzyme from the immobilized transducing antibody complex.

50 μl volumes of increasing concentrations of SP-A, the specific antigen, KLH, a non-specific antigen of 800 KD alton molecular weight and mouse immunoglobulin μ, IgM a non specific antigen of 1000 kD molecular weight from 6.25 to 100 μg ml$^{-1}$, diluted in wash buffer, were then loaded into duplicate wells. After 15 minutes, the supernatant was removed to assess release of enzyme from the complex by β-galactosidase substrate conversion. 50 μl volumes of the test were incubated with 50 gl of β-Galactosidase substrate buffer. Conversion from substrate to product was measured by optical density at 410 nm, indicating the presence of released enzyme in the supernatant.

Release of enzyme from the transduction complex was measured in the supernatant by β-galactosidase substrate conversion and measurement of product optical density at 410 nm. Only in the presence of SP-A, which has a molecular weight of 1200 kDaltons, and not in the presence of antigens of similar molecular weight KLH—800 kD and Ig M—1000 kDaltons was enzyme released. The effect is titratable and, at higher concentrations of SP-A, a saturation effect is noted.

In this format, the GAL 30.19 transducing antibody detects a minimum of 6.25 μg ml$^{-1}$ SP-A.

EXAMPLE 2

Purified Bispecific Immunoglobulin Assay

Demonstrating enzyme release in the presence of specific antigen (See FIG. 4).

Purified GAL30.19 immunoglobulin was coated at 20 μg per ml in ELISA coating buffer, carbonate/bicarbonate pH9.6, 50 μl per well, overnight at 4° C. Plates were blocked with 100 μl per well of 10% (v/v) FCS in PBS, 2 hours at room temperature. Wells were then incubated with 50 μl of 20 μg per ml of beta galactosidase (Sigma G5635) in wash buffer, PBS with 0.5% (w/v) bovine serum albumen (Sigma A7888), for 1 hour at room temperature. Wells were then washed with 2 washes of PBS Tween, to remove unbound enzyme from the immobilized Transducing Antibody complex.

50 μl volumes of increasing concentrations of SP-A, the specific antigen, and KLH, the non-specific antigen of equivalent molecular weight, from 6.25–100 μg per ml diluted in wash buffer, were then loaded into duplicate wells. After 15 minutes the supernatant was removed to assess release of enzyme from the complex by beta galactosidase substrate conversion.

Briefly, 50 μl volumes of the test were incubated with 50 μl of β-galactosidase substrate buffer. Conversion of substrate to product was measured by optical density at 410 nm, indicating the presence of released enzyme in the supernatant. Significant release of beta galactosidase from the transducing complex only occurs in the presence of the specific antigen SP-A, and not in the presence of an antigen of similar molecular weight, KLH.

EXAMPLE 3

Demonstrating Purified Bispecific Immunoglobulin Assay One-Step Antibody-Mediated Signal Transduction (See FIG. 5).

Transducing antibody complex was prepared as above and unbound beta galactosidase washed from the plates by two washes of PBS Tween. Simultaneous enzyme release on specific antigen detection was then demonstrated as follows:

50 μl volumes of increasing concentrations of SP-A, the specific antigen, and KLH, the non-specific antigen of equivalent molecular weight, were prepared from 6.25–100 μg per ml diluted in wash buffer and mixed with 50 μl volumes of beta galactosidase substrate buffer. The 100 μl samples of mixed antigen and beta galactosidase substrate were then added to wells containing the immobilized transducing antibody complex. Enzyme activity, from release of beta galactosidase from the complex, was measured by optical density at 410 nm, colour being produced by enzyme mediated product formation.

Product formation was measured immediately following addition of samples (0') and at ten minutes (10'). In both cases, only presence of the specific antigen SP-A, recognized by GAL30.19, results in significant product formation. This clearly indicates that for GAL 30.19 homogeneous immunoglobulin, antigen detection results in enzyme release in a one step manner, with signal transduction of inactive bound enzyme to active beta galactosidase capable of substrate conversion.

I claim:

1. A method of delivering an antigen to a patient comprising the steps of:

administering to a patient a first antigen bound to a first antigen binding site of an antibody having a first and second antigen binding site, wherein the patient's body contains a second antigen, wherein binding of the second antigen to the second antigen binding site of the antibody causes release of the first antigen from the first antigen binding site.

2. The method of claim 1 wherein the first antigen is selected from the group consisting of a therapeutic agent and a cosmetic agent.

3. The method of claim 1 wherein the first antigen is inactive when bound to the first antigen binding site and is active when released from the first antigen binding site.

4. The method of claim 3 wherein the first antigen is selected from the group consisting of a drug, an enzyme, and a cosmetic agent.

5. The method of claim 1 wherein after release of the first antigen from the first antigen binding site the first antigen or a reaction product of the first antigen binds to a third antigen binding site, wherein the binding to the third antigen binding site causes release of a prebound third antigen from an adjacent fourth antigen binding site.

6. A kit comprising:

a first antibody having a first and a second antigen binding site for a first and a second antigen, respectively;

a second antibody having a third and fourth antigen binding site; wherein the first antigen is a diagnostic marker and the second antigen is an enzyme; wherein the second antigen is enzymatically inactive when bound to the second antigen binding site; wherein the second antigen is released in an active form when the first antigen binds to the first antigen binding site; wherein a reaction product of the enzyme binds to the third antigen binding site and the binding at the third antigen binding site causes the release of a drug from the fourth antigen binding site.

7. The kit of claim 6 further comprising:

the second antigen which is prebound to the second antigen binding site.

8. The kit of claim 6 further comprising:

the drug which is prebound to the fourth antigen binding site.

9. The kit of claim 8 wherein the second antigen and the drug are prebound to the second antigen binding site and the fourth antigen binding site, respectively.

10. The kit of claim 6 wherein the drug is inactive when bound to the second antibody.

11. A trispecific antibody comprising:

a first antigen binding site directed to a diagnostic marker;

a second antigen binding site directed to an enzyme; and a third antigen binding site directed to and bound to a drug or other therapeutic agent, wherein the drug or other therapeutic agent is inactive when bound, wherein upon binding of the diagnostic marker to the first antigen binding site the enzyme is released from the second antigen binding site and the therapeutic agent is released from the third antigen binding site.

12. A multi-specific antibody comprising:

a first antigen binding site directed to a first antigen which is a marker indicative of a disease or microorganism; and a second antigen binding site directed to a drug or other therapeutic agent; wherein binding of the first antigen to the first antigen binding site causes release of the drug or other therapeutic agent from the second antigen binding site.

13. The antibody of claim 12 wherein the drug or other therapeutic agent is inactive when bound.

14. A therapeutic method comprising the steps of:

administering to a patient one or two multi-specific antibodies having a first, second, third, and fourth antigen binding site, wherein a first and a second prodrug are bound at the first and second antigen binding sites, wherein upon binding of a first and a second diagnostic marker molecule to the third and fourth antigen binding sites the two prodrugs are released, wherein the first and second prodrugs are active only when released in each other's presence.

* * * * *